(12) United States Patent
Mochitate (10) Patent No.: US 8,781,061 B2
(45) Date of Patent: Jul. 15, 2014

(54) X-RAY CT ROTARY APPARATUS

(75) Inventor: Mikio Mochitate, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 246 days.

(21) Appl. No.: 13/263,218

(22) PCT Filed: Apr. 13, 2010

(86) PCT No.: PCT/JP2010/056553
§ 371 (c)(1),
(2), (4) Date: Oct. 6, 2011

(87) PCT Pub. No.: WO2010/119850
PCT Pub. Date: Oct. 21, 2010

(65) Prior Publication Data
US 2012/0027163 A1 Feb. 2, 2012

(30) Foreign Application Priority Data

Apr. 16, 2009 (JP) .................. 2009-100226

(51) Int. Cl.
*H05G 1/02* (2006.01)
*H05G 1/04* (2006.01)
(52) U.S. Cl.
USPC ............................ 378/4; 378/189; 378/193
(58) Field of Classification Search
CPC ..... H05G 1/02; H05G 1/04; H05H 2007/002; A61B 2019/2261; B25J 9/0009; B25J 9/1615
USPC ............ 378/4–20, 189, 193, 194, 204, 210
See application file for complete search history.

(56) References Cited

U.S. PATENT DOCUMENTS 5,761,269 A 6/1998 Sugihara et al.
6,314,157 B1 * 11/2001 Tachizaki ..................... 378/4
(Continued)

FOREIGN PATENT DOCUMENTS

| JP | 9-47448 | 2/1997 |
|---|---|---|
| JP | 9-56710 | 3/1997 |
| JP | 2005-536288 | 12/2005 |
| JP | 2007-37873 | 2/2007 |

OTHER PUBLICATIONS

International Search Report in PCT/JP2010/056553, May 18, 2010.

*Primary Examiner* — Anastasia Midkiff
(74) *Attorney, Agent, or Firm* — Cooper & Dunham LLP (57) ABSTRACT

In order to provide an X-ray CT apparatus including a rotating portion capable of enduring a high speed rotation and tilting, the rotating portion includes a cylinder portion 42, a ring portion 41 that is disposed at a position which is offset from the center in the direction of a rotation axis 32 of the cylinder portion 42, and the cylinder portion 42 and the ring portion 41 are supported by spoke portions 43 to 46. An X-ray tube and one or more circuit units are fixed on the inner wall of the cylinder portion 42. Thereby, the centers of gravity of an X-ray detection unit and the circuit units can be positioned at the center position in the direction of the rotation axis 32 of the cylinder portion 42. Since the centrifugal force of the X-ray detection unit or the like can be supported in the vicinity of the center in the direction of the axis 32 of the cylinder portion 42, distortion of the cylinder portion 42 is not easily generated, and the rotating portion capable of enduring the high speed rotation or the tilting can be provided.

10 Claims, 9 Drawing Sheets

(56) References Cited

U.S. PATENT DOCUMENTS

| | | |
|---|---|---|
| 7,447,294 B2 * | 11/2008 | Sadotomo et al. ............... 378/4 |
| 2004/0170254 A1 | 9/2004 | Gregerson et al. |
| 2006/0120511 A1 | 6/2006 | Gregerson et al. |
| 2010/0027758 A1 * | 2/2010 | Luecke et al. ............... 378/197 |
| 2010/0027759 A1 * | 2/2010 | Luecke et al. ............... 378/197 |

* cited by examiner

(a) FRONT SURFACE (b) REAR SURFACE

X-RAY CT ROTARY APPARATUS

FIELD OF THE INVENTION

The present invention relates to an X-ray CT apparatus capable of scanning with high speed, and particularly, to a rotating frame.

DESCRIPTION OF RELATED ART

In an X-ray CT apparatus of the related art, for rotating an X-ray tube unit, an X-ray detection unit, a cooling unit, or the like around an object to be examined, in general, these are mounted on a disk-shaped rotating portion, and the entire disk-shaped rotating portion is rotated. In order to fix the X-ray tube unit or the like to the rotating portion, fixing means such as a fixing bolt or a bracket is used. However, when the rotating portion is rotated, since not only the self weight of the X-ray tube unit or the like but also a load due to centrifugal force are applied to the fixing bolt or the like, particularly, in the case of a high speed rotation, there is a problem in that a great load is applied to the fixing bolt or the like.

Thus, in PTLs 1 and 2, the following configurations are suggested. That is, a cylinder is fixed along the periphery of a disk and the X-ray tube unit or the like is fixed on the inner wall surface of the cylinder, and therefore, load due to centrifugal force is supported by the cylinder, and load of the fixing bolt is reduced. In the configurations, the disk is positioned at a substantial center position of the cylinder in the direction of a rotation axis, that is, so as to partition the center in the thickness direction of the cylinder. Moreover, in PTL 2, an opening having a shape which is fitted to the X-ray tube unit or the like is installed in the disk, and the X-ray tube unit or the like is inserted in the opening of the disk. Thereby, the disk is constituted so as to support weight of the X-ray tube unit and a portion of the centrifugal force.

PATENT LITERATURE

PTL 1: JP-A-2000-116641
PTL 2: U.S. Pat. No. 6,314,157

SUMMARY OF INVENTION

In the PTLs 1 and 2, since the disk is disposed so as to partition the substantial center in the axis direction of the cylinder, a photographing surface (an X-ray transmitting surface) can not coincide with the disk position. Accordingly, it is necessary to dispose parts to be mounted on the disk such as the X-ray tube unit or the X-ray detection unit so as to be offset from the center in the axis direction of the cylinder, and the center of gravity of the X-ray tube or the like is offset from the disk. Therefore, moments of an out-of-plane load and the centrifugal force are applied to the disk. Since these moments act in the direction in which the disk is to be bent, in order to secure the strength and stiffness of the disk to endure the moments, the entire plate thickness of the disk increases and the weight also increases.

Particularly, in recent years, since multi-slicing has progressed and the size of the X-ray detection unit is longer in the direction of the rotating axis, deviation amounts of the center of gravity of the X-ray detection unit and the center of gravity of the X-ray tube unit corresponding thereto from the disk become great, and the moments of the out-of-plane load and the centrifugal force applied to the disk tend to become great. In addition, the moments become greater as the rotation speed becomes higher.

When using a measurement method in which the photographing surface is tilted with respect to the body axis of the object, it is necessary to rotate the X-ray tube unit and the X-ray detection unit or the like in the state where those are tilted. When the rotating surface is tilted, if the configurations of the PTLs 1 and 2 are adopted, since the gravity of the X-ray tube unit or the like is applied to the disk in the direction in which the disk is tilted, the moment in the direction in which the disk is bent is further increased.

An object of the invention is to provide an X-ray CT apparatus including a rotating portion capable of enduring a high speed rotation and tilting.

Solution to Problem

According to the invention for accomplishing the object, the following X-ray CT apparatus is provided. That is, in an X-ray CT apparatus including an X-ray tube, an X-ray detection unit, one or more circuit units, and a rotating portion on which the X-ray tube, the X-ray detection unit, and one or more circuit units are mounted to be rotated, the rotating portion includes a cylinder portion in which the X-ray tube and one or more circuit units are fixed on the inner wall thereof, a ring portion that is disposed so as to be near to one opening rather than the center in the axis direction of the cylinder portion and that has an opening for inserting an object, and plural spoke portions that connect the cylinder portion and the ring portion. In this way, due to the fact that the ring portion is disposed in the position which is offset from the center in the direction of the rotation axis of the cylinder portion and supported by the spoke portions, the centers of gravity of the X-ray detection unit or the circuit units can be positioned at the center position in direction of the rotation axis of the cylinder portion. Thereby, distortion is not easily generated in the cylinder portion, and the rotating portion capable of enduring a high speed rotation and tilting can be provided.

The ring portion may be positioned at the position of one opening of the cylinder portion. Thereby, the inner space of the cylinder portion can be secured with the maximum width.

The X-ray tube and one more circuit unit may be constituted so that each end is inserted into the opening between the spoke portions. Thereby, even an X-ray tube or the like which is long in the direction of the rotation axis can be mounted on the cylinder portion. In this case, the X-ray tube and one or more circuit units may be disposed without contacting the spoke portions and the ring portion.

It is preferable that stiffness of the spoke portions of both sides of the X-ray tube is configured to be greater than that of the other spoke portions. For example, the spoke portions of both sides of the X-ray tube use a portion in which the thickness in the direction of the rotation axis is thicker than those of the other spoke portions.

The plural spoke portions may include spoke portions of plural kinds in which the cross-sectional shapes are different in the direction perpendicular to a radial direction.

The ring portion may be constituted so as to have regions in which the width is wide in the radial direction, and the X-ray detection unit may be mounted on each region.

In addition, according to another aspect of the invention, the following X-ray CT apparatus is provided. That is, in an X-ray CT apparatus including an X-ray tube, an X-ray detection unit, one or more circuit units, and a rotating portion on which the X-ray tube, the X-ray detection unit, and one or more circuit units are mounted to be rotated, the rotating portion includes a cylinder portion in which the X-ray tube and one or more circuit units are fixed on the inner wall thereof, a ring portion on which the X-ray detection unit is fixed and that has an opening into which an object is inserted, and plural spoke portions that connect the cylinder portion and the ring portion.

Advantageous Effects of Invention

In the X-ray CT apparatus of the invention, since the X-ray tube or the like can be disposed at the center in the axis direction of the cylinder, distortion of the cylinder due to the centrifugal force applied to the X-ray tube is suppressed, and the rotating portion capable of enduring a high speed rotation and tilting can be provided.

DETAILED DESCRIPTION OF THE INVENTION

An X-ray CT apparatus of an embodiment of the invention will be described.

Figure 1:
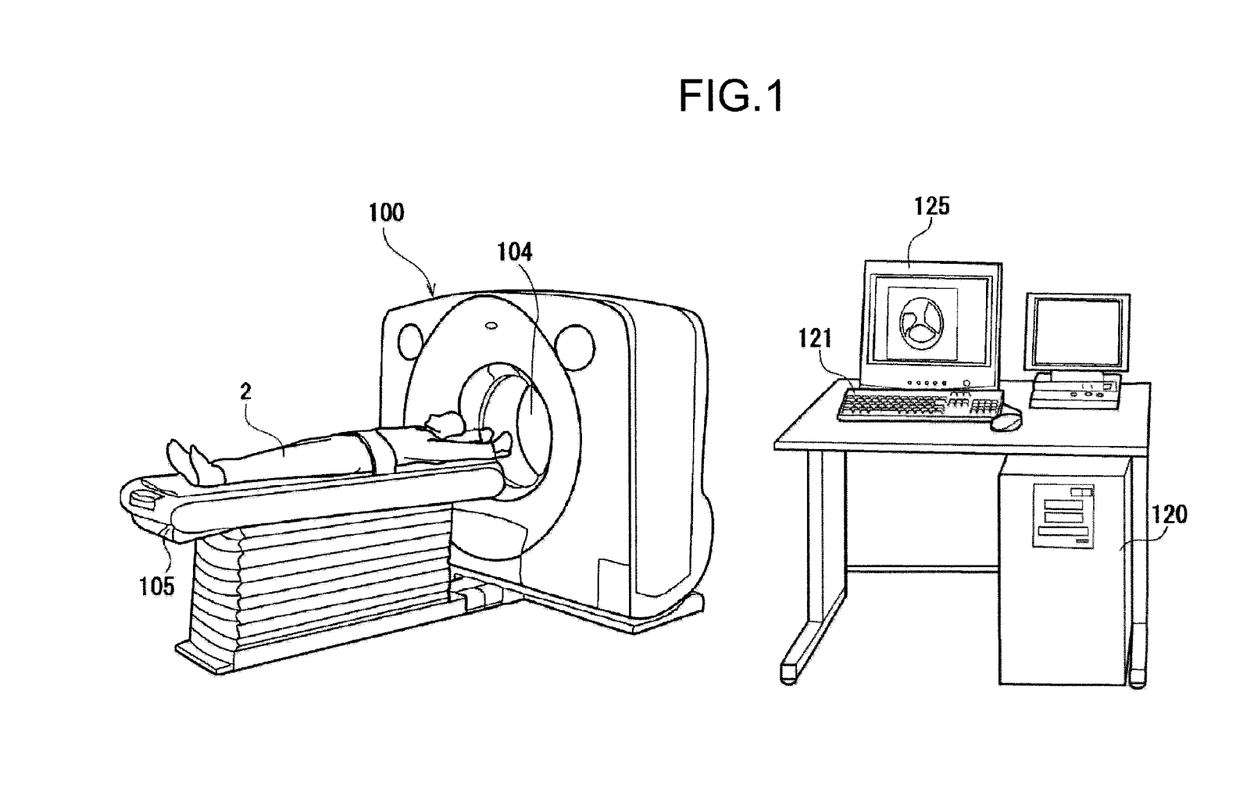
FIG. 1 is a perspective view explaining an overall outline of an X-ray CT apparatus of the present embodiment.
Figure 2:
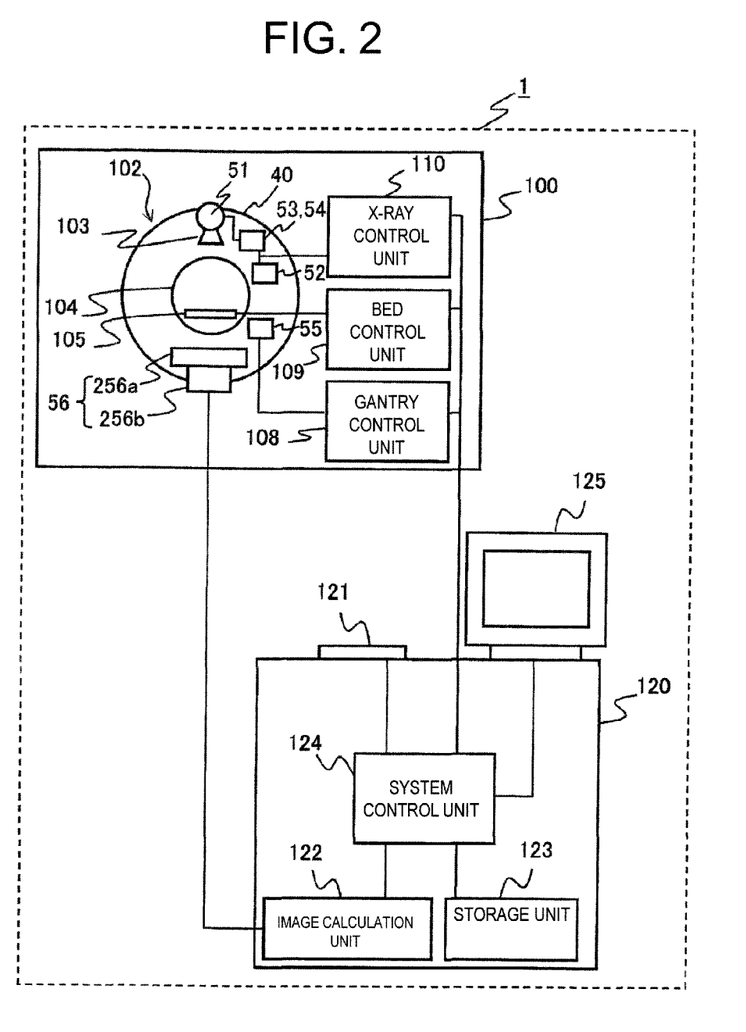
FIG. 2 a block diagram showing the overall configuration of the X-ray CT apparatus of the present embodiment.

First, the overall configuration of the X-ray CT apparatus of the present embodiment will be described with reference to FIGS. 1 and 2. FIG. 1 is an outline view of the X-ray CT apparatus 1, and FIG. 2 is a block diagram showing the overall configuration thereof. As shown in FIGS. 1 and 2, the X-ray CT apparatus 1 includes a gantry 100, a bed 105, and an operating unit 120.

The gantry 100 includes a rotating disk portion 102, a gantry control unit 108, a bed control unit 109, and an X-ray control unit 110.

The rotating disk portion 102 includes a rotating frame 40 having an opening 104 into which the object 2 disposed on the bed 105 enters, an X-ray tube 51 which is mounted on the rotating frame 40, a collimator 103, and an X-ray detection unit 56, and the rotating disk portion 102 rotates around the object 2. In addition, the rotating disk portion 102 includes a tilt mechanism which rotates the bed 105 in a state where a direction of a rotation axis is tilted with respect to a main plane of a top panel of the bed 105.

In addition, as shown in FIG. 1, the gantry 100 accommodates the rotating disk portion 102 or the like in the case.

The X-ray tube 51 is a unit which radiates the X-ray to the object 2 disposed on the bed 105. The collimator 103 is a unit which limits a radiation range of the X-ray radiated from the X-ray tube 51. The X-ray detection unit 56 includes an X-ray detector 256a and a data collection unit 256b. The X-ray detector 256a is a unit which is disposed so as to be opposite to the X-ray tube 51 on the rotating frame 40 and measures a space distribution of the transmitted X-ray by detecting the X-ray transmitted through the object. In the X-ray detector 256a, plural X-ray detection elements is arranged in the rotation direction of the rotating frame 40 or two-dimensionally in the rotating direction and the direction of the rotation axis of the rotating frame 40. The data collection unit 256b is a unit which collects the X-ray dose detected by the X-ray detector 256a as digital data.

The gantry control unit 108 is a unit which controls the rotation of the rotating disk portion 102, and a control portion 55, which is a portion of the gantry control unit 108, is mounted on the rotating frame 40. The bed control unit 109 is a unit which controls vertical and longitudinal movements of the bed 105.

The X-ray control unit 110 is a unit which controls power input into the X-ray tube 51, and high voltage generation units 53 and 54 and a cooling unit 52, which are a portion of the X-ray control unit 110, are mounted on the rotating frame 40.

The operating unit 120 includes an input unit 121, an image calculation unit 122, a display unit 125, a storage unit 123, and a system control unit 124. The input unit 121 is a unit which inputs a name of the object, a scan date, a photographing condition, or the like, and specifically, is a key board or a pointing unit. The image calculation unit 122 is a unit which calculates the measured data sent from the data collection unit 256b of the X-ray detection unit 56 and reconstructs a CT image. The display unit 125 is a unit which displays the CT image prepared by the image calculation unit 122, and specifically, is a CRT (Cathode-Ray Tube) or a liquid crystal display, or the like. The storage unit 123 is a unit which stores the data collected by the data collection unit 256b and image data of the CT image prepared by the image calculation unit 122, and specifically, is an HDD (Hard Disk Drive) or the like. The system control unit 124 is a unit which controls those units, the gantry control unit 108, the bed control unit 109, and the X-ray control unit 110.

The mechanical configuration of the gantry 100 will be described in detail with reference to FIGS. 3 to 6.

Figure 3:
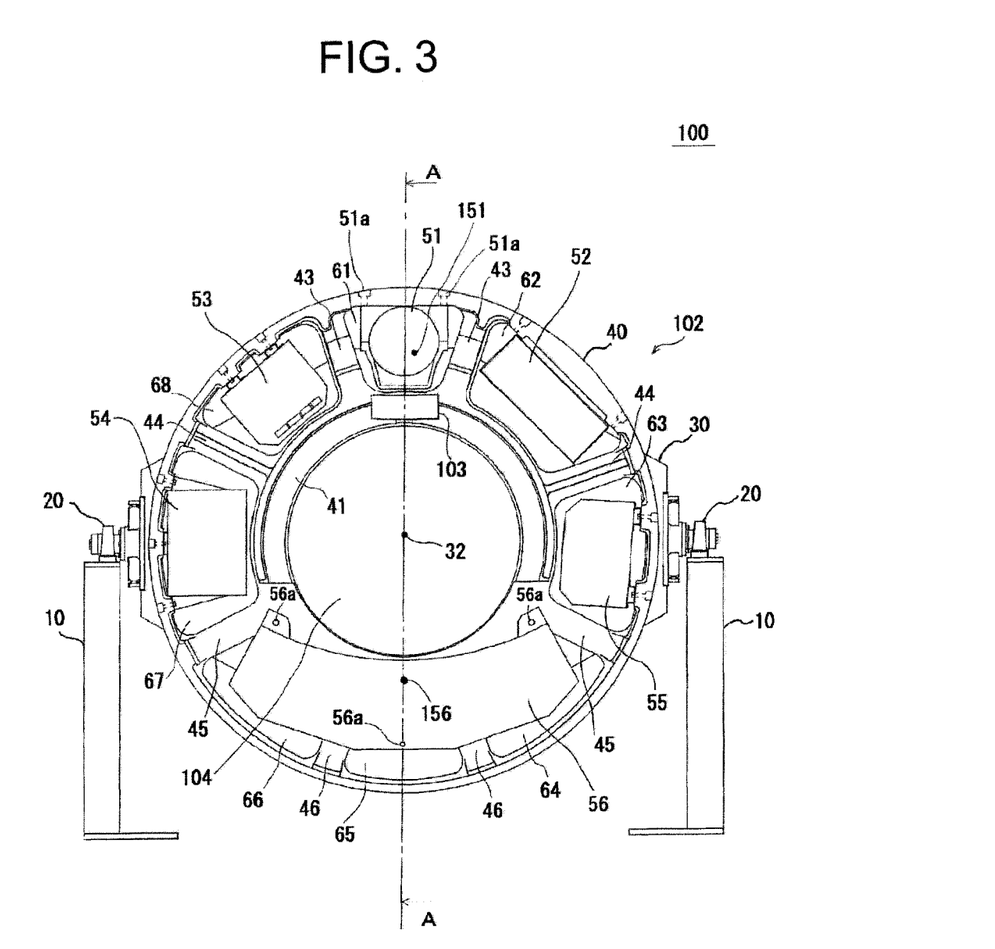
FIG. 3 is a front view showing a gantry 100 in which the case of the X-ray CT apparatus of the present embodiment is removed.
Figure 4:
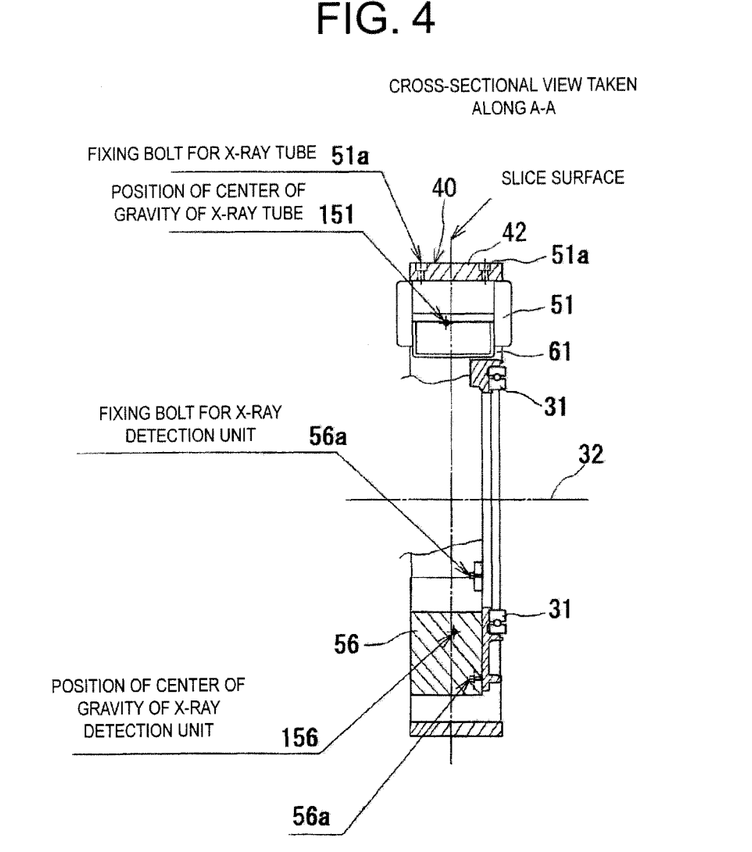
FIG. 4 is a cross-sectional view taken along a line A-A of the gantry 100 of FIG. 3.
Figure 5:
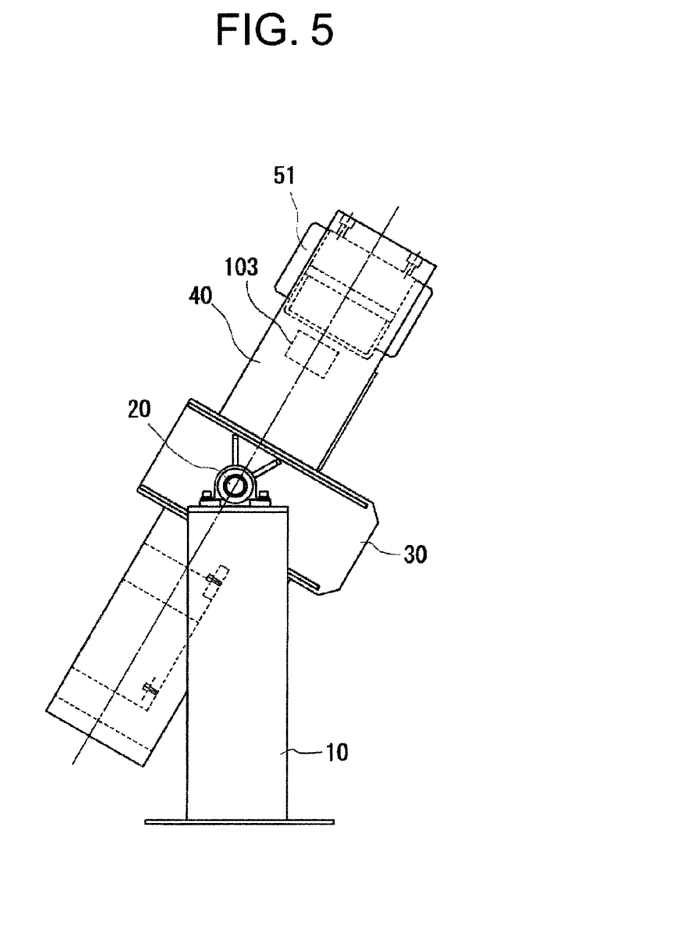
FIG. 5 is a side view showing a state where the gantry 100 of FIG. 3 is tilted.
Figure 6:
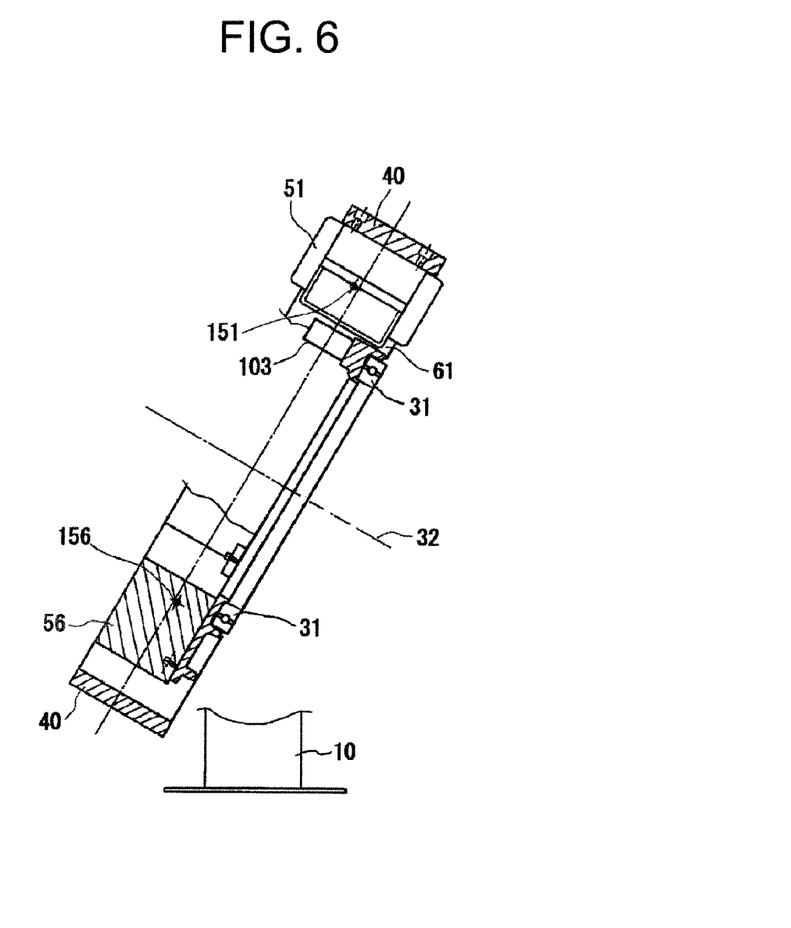
FIG. 6 is a cross-sectional view showing a state where the gantry 100 of FIG. 3 is tilted.

FIG. 3 is a front view showing the gantry 100 in which the case is removed, FIG. 4 is a cross-sectional view taken along a line A-A of FIG. 3, FIG. 5 is a side view showing the tilted gantry 100, and FIG. 6 is a cross-sectional view showing the tilted gantry 100. The gantry 100 includes a stand 10 for rotatably supporting the rotating disk portion 102, a bearing 20, and a main frame 30. The main frame 30 is supported by the stand 10 via the bearing 20 and can be driven so as to be tilted with respect to the main plane of the top panel of the bed 105. The rotating frame 40 of the rotating disk portion 102 is rotatably supported by the main frame 30 via the bearing 31. The rotating frame 40 is driven to be rotated by a rotation drive source (not shown).

A photographing operation of the X-ray CT apparatus will be briefly described. Due to the fact the X-ray control unit 110 controls power, which is input to the X-ray tube 51, based on a photographing condition input from the input unit 121, particularly, a voltage of the X-ray tube, current of the X-ray tube, or the like, the X-ray tube 51 radiates the X-ray to the object according to the photographing condition. The X-ray detection unit 56 detects the X-ray transmitting the object radiated from the X-ray tube 51 through plural X-ray detection elements of the X-ray detector 256a, and measures the distribution of the transmitted X-ray. The rotation speed or the angle of the rotation axis (tilt) or the like of the rotating disk portion 102 is set to the photographing condition, which is input from the input unit 121, by the gantry control unit 108. The bed 105 is controlled by the bed control unit 109 and is operated based on the photographing condition input from the input unit 121, particularly, a screw pitch or the like.

By repeatedly performing the measurement of the X-ray radiation from the X-ray tube 51 and the measurement of the distribution of the transmitted X-ray by the X-ray detection unit 56 along with the rotation of the rotating disk portion 102, projection data from various angles are obtained by the data collection unit 256b. The projection data from the obtained various angles are sent to the image calculation unit 122. Due to the fact that the image calculation unit 122 performs a back-projection processing of projection data from the sent various angles, the CT image is reconstructed. The reconstructed and obtained CT image is displayed to the display unit 125.

Figure 7:
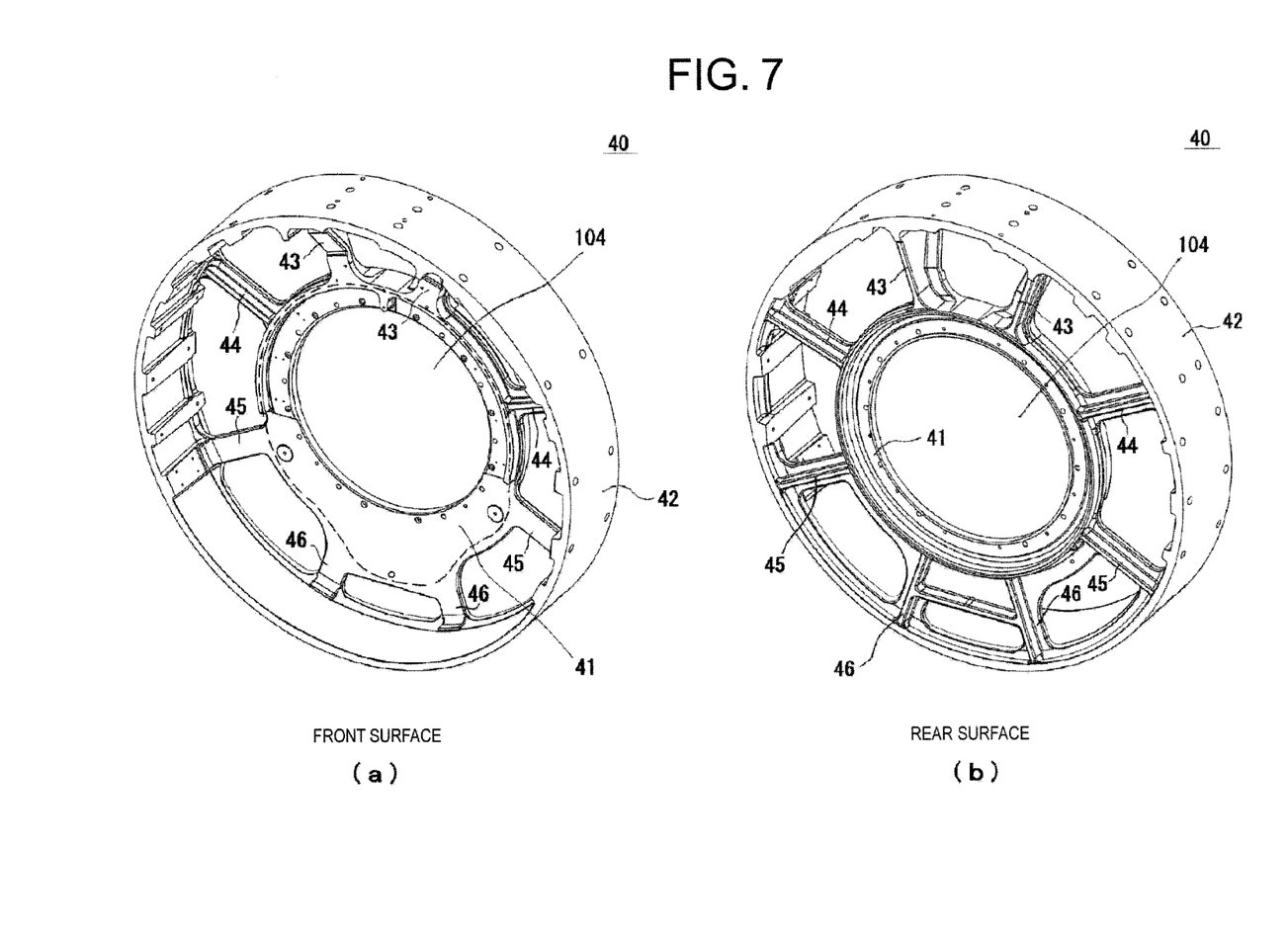
FIG. 7(a) is a perspective view showing a front surface side of a rotating frame 40 of the X-ray CT apparatus of the present embodiment.
FIG. 7(b) is a perspective view showing a rear surface side thereof.

The detailed shape of the rotating frame 40 according to the present embodiment will be described with reference to FIGS. 7 to 9. FIG. 7(a) is a perspective view when viewing the rotating frame 40 from the front surface side (the side on which the X-ray detection unit 56 or the like is mounted), and FIG. 7(b) is a perspective view when viewing the rotating frame 40 from the rear surface side, FIG. 8 is a front view and a partial cross-sectional view of the rotating frame 40, FIG. 9(a) is a front view of the rotating frame 40, FIG. 9(b) is a cross-sectional view taken along a line B1-B3 of FIG. 9(a), and FIG. 9(c) is a cross-sectional view taken along a line C1-C3 of FIG. 9(a).

Figure 8:
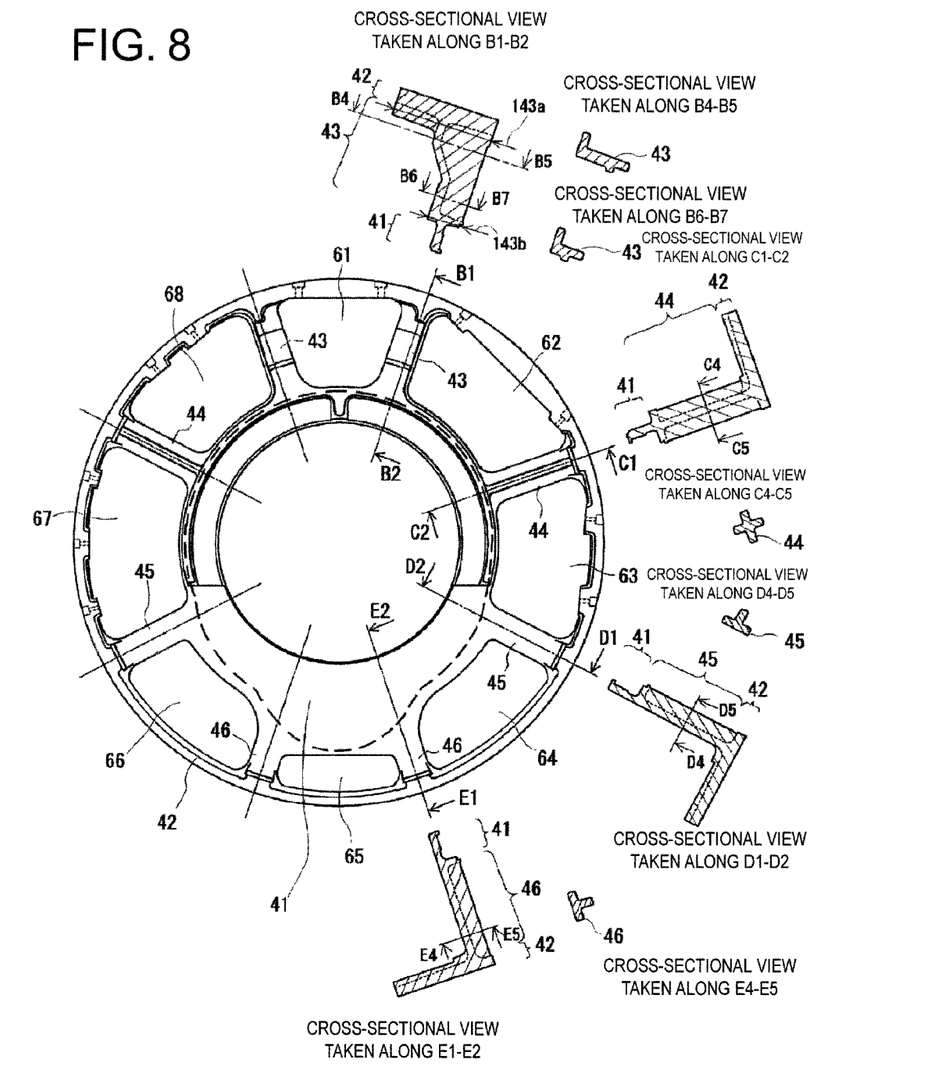
FIG. 8 is a front view and a partial cross-sectional view showing the rotating frame 40 of the X-ray CT apparatus of the present embodiment.
Figure 9:
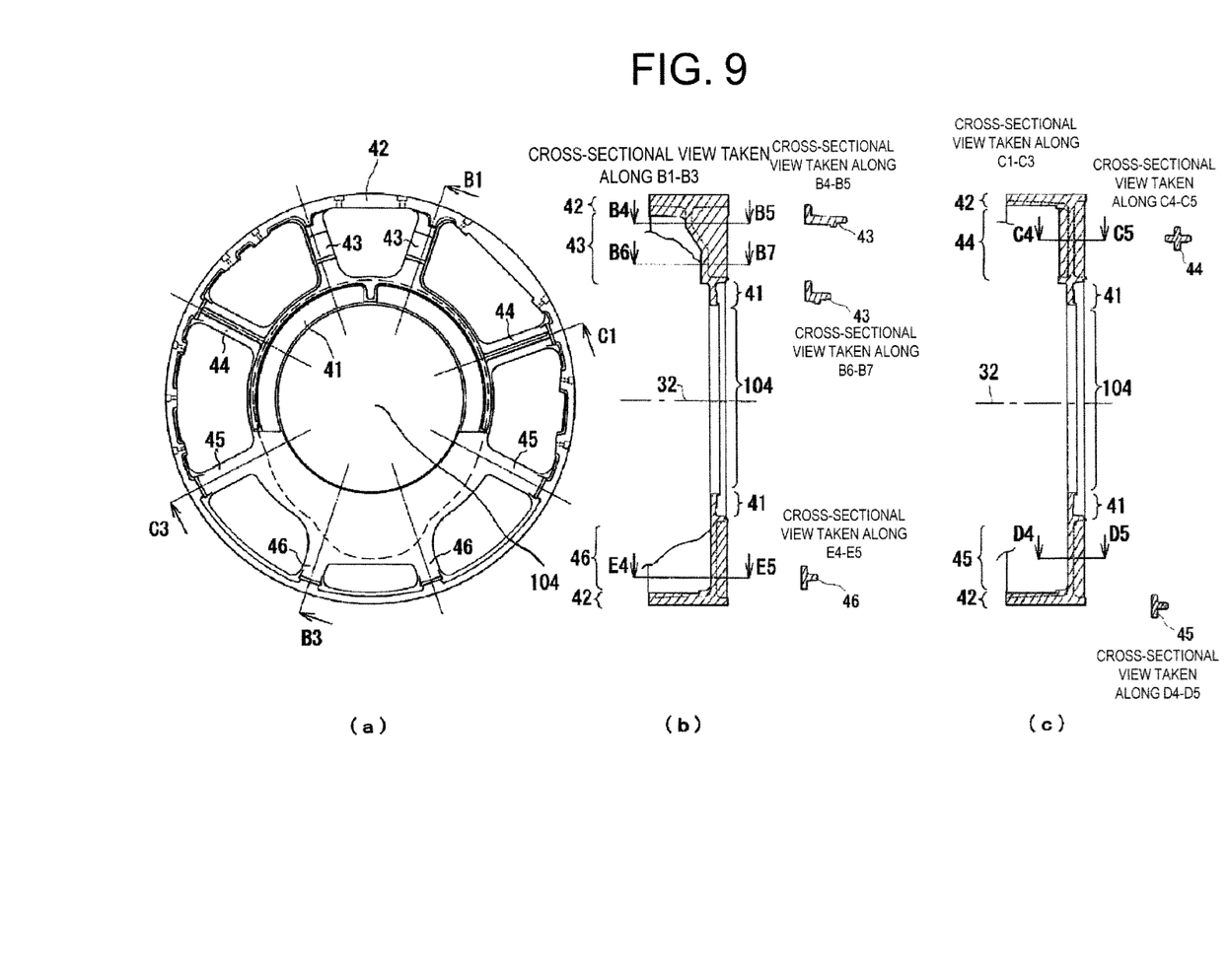
FIG. 9(a) is a front view showing the rotating frame 40 of the X-ray CT apparatus of the present embodiment.
FIG. 9(b) is a cross-sectional view taken along a line B1-B3 of FIG. 9(a)
FIG. 9(c) is a cross-sectional view taken along a line C1-C3 of FIG. 9(a).

As shown in FIGS. 7 to 9, the rotating frame 40 is constituted by a ring portion 41 which is disposed at the periphery of the opening 104 into which the object 2 is inserted, a cylinder portion 42, and eight radial spoke portions 43 to 46 which connect the ring portion 41 and the cylinder portion 42. The eight spoke portions 43 to 46 include spokes of four kinds of shapes, of which there are two of each, and openings 61 to 68 are each formed between the spoke portions.

As shown in FIGS. 9(b) and 9(c), the position, in which the ring portion 41 is disposed, substantially coincides with the opening of the rear surface side of the cylinder portion 42 in the direction of the rotation axis 32. Due to the fact that the ring portion 41 is disposed at the rear surface side of the cylinder portion 42, a wide inner space of the cylinder portion 42 is secured. Thereby, it is possible to set the X-ray transmitting surface (slice surface) to the center portion in the direction of the rotation axis 32 of the cylinder portion 42.

As shown in FIGS. 3 and 4, the X-ray tube 51 is disposed at the space of the front surface side of the opening 61 between two spoke portions 43 of the same kind which are disposed to be adjacent to each other. The X-ray tube 51 is fixed on the inner wall surface of the cylinder portion 42 by bolts 51a. The end of the rear surface side of the X-ray tube 51 is inserted into the opening 61. The end of the rear surface side does not come into contact with the edge of the opening 61 other than the cylinder portion 42, in other words, does not contact either side of the spoke portions 43 or the ring portion 41.

The cooling unit 52, the control portion 55, and the high voltage generation units 53 and 54 are each disposed at the spaces of the front surface sides of the openings 62, 63, 67, and 68, and are fixed on the inner surface of the cylinder portion 42 by bolts. The ends of the rear surface sides of the cooling unit 52, control portion 55, and the high voltage generation units 53 and 54 are each inserted into the openings 62, 63, 67, and 68, but do not contact either side of the spoke portions or the ring portion 41.

The fixation of the X-ray tube 51, the cooling unit 52, the control portion 55, the high voltage generation units 53 and 54 to the cylinder portion 42 by bolts is performed so that the axis directions of the bolts are substantially facing toward the radial direction of the cylinder portion 42. Thereby, the bolts do not receive the loads of the mounted parts by the centrifugal force which is applied to the X-ray tube 51 or the like due to high speed rotation of the cylinder portion 42, and the inner wall of the cylinder portion 42 can receive the centrifugal force of the mounted parts.

In addition, as understood from FIG. 7(a), in the inner wall surface of the cylinder portion 42, the portions for fixing the X-ray tube 51, the cooling unit 52, the control portion 55, and the high voltage generation units 53 and 54 with bolts are formed as a pedestal-shape, and the other portions are formed as a concave-shape. By this configuration, the strength of the bolt fixation is not affected and the weight of the cylinder portion 42 can be reduced.

Next, the shapes of the spoke portions 43 to 46 will be described. Considering the standpoints of deformation prevention during the rotation and the weight reduction, the shapes of the spoke portions are designed so as to be different to one another. That is, if portions from the X-ray tube 51 to the X-ray detection unit 56 in the rotating frame 40 are deformed during rotating, deviation occurs in a geometry system of the X-ray transmitting surface or the like and the photographing accuracy is affected. Therefore, the shapes of the portions are designed to have great stiffness so that deformation is not generated. On the other hand, the other portions are designed for weight reduction.

Specifically, as shown in a cross-sectional view taken along a line B1-B2 in FIG. 8 and a cross-sectional view taken along a line B1-B3 in FIG. 9(b), in the spoke portions 43 disposed at both sides of the X-ray tube 51, a thickness 143a of a portion connecting to the cylinder portion 42 in the direction of the rotation axis 32 is set to be the same as the thickness of the cylinder portion 42 in the direction of the rotation axis 32. Thereby, the stiffness of the portion supporting the X-ray tube 51 of the cylinder portion 42 is enhanced, and the portion is designed so as to not be deformed during rotating. In addition, the thickness of spoke portion 43 in the direction of the rotation axis 32 is thinned in stages approaching the ring portion 41, and is reduced to a thickness 143b which is close to the thickness of the ring portion 41 at the portion connecting to the ring portion 41. In addition, as shown in a cross-sectional view taken along a line B4-B5 of FIG. 8 and a cross-sectional view taken along a line B6-B7 of FIG. 8, in the width in the circumferential direction of the spoke portions 43, the width of the front surface side is wide, the width of the rear surface side is narrow, and the spoke portions 43 have a three-dimensional shape. Thereby, the stiffness is enhanced, the thickness of the portion which does not contribute to the stiffness is reduced, and weight reduction of the spoke portions 43 is improved.

Since the portion on which the X-ray detection unit 56 is mounted needs a wide attachment surface in the radial direction and the circumferential direction, as shown in FIG. 8, the width in the radial direction of the ring portion 41 is wide, and therefore, the stiffness is also enhanced. Two of the spoke portions 45 and 46, which connect the ring portion 41 having a wide width to the cylinder portion 42, are disposed so as to be symmetrical at the left and the right of the center of the X-ray detection unit 56 respectively. In order not to disturb the disposition of the X-ray detection unit 56, and the spoke portions 45 and 56 are formed so that the thickness in the rotation axis 32 is thin and the attachment surface of the ring portion 41 is extended. Thereby, as shown in a cross-sectional view taken along a line D4-D5 and a cross-sectional view taken along a line E4-E5, the cross-sectional shapes of the spoke portions 45 and 46 are formed in a T-shape in order to enhance the stiffness and improve the weight reduction.

As shown in FIG. 3, the X-ray detection unit 56 is fixed by bolts 56a in the region which is formed as a plane shape so that the width in the radial direction of the ring portion 41 is wide. The direction of the axes of the bolts 56a is the direction of the rotation axis 32.

On the other hand, as shown in FIG. 3, the spoke portions 44 each are disposed between the cooling unit 52 and the control portion 55 and between the high voltage unit 53 and 54. The spoke portions 44 are the portions which do not affect the axis direction of the X-ray. Thereby, as shown in a cross-sectional view taken along a line C1-C2 of FIG. 8 and a cross-sectional view of FIG. 9(c), the thickness of the spoke portion 44 is constant in the direction of the rotation axis 32, and the weight reduction is improved. In addition, as shown in a cross-sectional view taken along C4-C5 of FIG. 8, the cross-sectional shape of the spoke portion 44 is formed in a cross shape, and therefore, the stiffness is enhanced.

In the present embodiment, the ring portion 41, the cylinder portion 42, and the spoke portions 43 to 46 are integrally constituted by a casting, and therefore, the stiffness is enhanced.

In this way, according to the present embodiment, the ring portion 41 to which the driving source rotating the rotating frame 40 is connected is disposed at the opening surface of the rear surface side of the cylinder portion 42, and the ring portion 41 and the cylinder portion 42 are connected to each other by four kinds of spoke portions 43 to 46 having different shapes. Therefore, the space of the inner portion of the cylinder portion 42 is widely secured. Thereby, the X-ray transmitting surface (slice surface) from the X-ray tube 51 to the X-ray detection unit 56 can be positioned at the center of the cylinder portion 42 with respect to the direction of the rotation axis 32. Therefore, even when multi-slice is performed, plural X-ray transmitting surfaces can be secured in the center portion of the cylinder portion 42. In addition, as shown in FIG. 4, the center of gravity 151 of the X-ray tube 51 and the center of gravity 156 of the X-ray detection unit 56 are positioned in the vicinity of the X-ray transmitting surface, that is, the center in the direction of the rotation axis 32 of the cylinder portion 42 according to their structures. Therefore, the centrifugal force is applied to the center of the direction of the rotation axis 32 with respect to the cylinder portion 42, the moment in the direction which distorts the cylinder portion 42 is small, and the distortion does not easily occur.

In addition, among four kinds of spoke portions 43 to 46 having different shapes, two spoke portions 43 having great stiffness are symmetrically disposed at both arms of the X-ray tube 51, and two spoke portions 45 and 46 are disposed symmetrically at the left and the right of the center line of the X-ray detection unit 56 respectively. Thereby, the stiffness is focused in the direction of the X-ray transmitting surface which connects the X-ray detection unit 56 from the X-ray tube 51, and the weight reduction is improved in the other directions. Therefore, the geometry system of the X-ray transmitting surface is supported by great stiffness, and the weight reduction is improved.

Thus, in the X-ray CT apparatus of the present embodiment, the rotating disk portion 102 can be rotated at high speed or in a state where the rotation axis is tilted with respect to the object. In addition, even in the above cases, it is possible to prevent the geometry system of the X-ray transmitting surface of the rotating frame 40 from distorting, and the CT photographing can be performed in the multi-slice with high accuracy.

In the present embodiment described above, the rotating frame 40 is constituted so as to include eight spoke portions 43 to 46. However, the number of the spoke portions is not limited to eight. That is, more than eight spoke portions or less than eight spoke portions can be provided considering the stiffness or the weight reduction which is necessary according to the rotation speed or like.

DESCRIPTION OF REFERENCE NUMERALS

1: X-RAY CT APPARATUS
10: STAND
20: BEARING
30: MAIN FRAME
40: ROTATING FRAME
41: RING PORTION
42: CYLINDER PORTION
43 TO 46: SPOKE PORTIONS
51: X-RAY TUBE
52: COOLING UNIT
53 AND 54: HIGH VOLTAGE GENERATION UNIT
55: CONTROL PORTION
56: X-RAY DETECTION UNIT
100: GANTRY
102: ROTATING DISK PORTION
103: COLLIMATOR
104: OPENING
105: BED
108: GANTRY CONTROL UNIT
109: BED CONTROL UNIT
110: X-RAY CONTROL UNIT
120: OPERATING UNIT
121: INPUT UNIT
122: IMAGE CALCULATION UNIT
123: STORAGE UNIT
124: SYSTEM CONTROL UNIT
125: DISPLAY UNIT
256a: X-RAY DETECTOR
256b: DATA COLLECTION UNIT

The invention claimed is:

1. An X-ray CT apparatus comprising an X-ray tube, an X-ray detection unit, one or more circuit units, and a rotating portion on which the X-ray tube, the X-ray detection unit, and one or more circuit units are mounted to be rotated,
wherein the rotating portion includes a hollow cylinder portion in which the X-ray tube and one or more circuit units are fixed on an inner wall thereof, a ring portion that is disposed so as to be near to one opening rather than the center in an axis direction of the hollow cylinder portion and that has an opening for inserting an object to be examined, and a plurality of spoke portions that connect the hollow cylinder portion and the ring portion, and
wherein the ring portion includes a region in which the width is wider than the remainder of the ring portion, and the X-ray detection unit is mounted on the region.

2. The X-ray CT apparatus according to claim 1,
wherein the ring portion is positioned at the position of one opening of the hollow cylinder portion.

3. The X-ray CT apparatus according to claim 1,
wherein the X-ray tube and one or more circuit units are constituted so that each end thereof is inserted into an opening between the spoke portions.

4. The X-ray CT apparatus according to claim 3,
wherein the X-ray tube and one or more circuit units are disposed without contacting the spoke portions and the ring portion.

5. The X-ray CT apparatus according to claim 3,
wherein stiffness of the spoke portions on both sides of the X-ray tube is configured to be greater than that of the other spoke portions.

6. An X-ray CT apparatus comprising an X-ray tube, an X-ray detection unit, one or more circuit units, and a rotating portion on which the X-ray tube, the X-ray detection unit, and one or more circuit units are mounted to be rotated,
wherein the rotating portion includes a hollow cylinder portion in which the X-ray tube and one or more circuit units are fixed on an inner wall thereof, a ring portion that is disposed so as to be near to one opening rather than the center in an axis direction of the hollow cylinder portion and that has an opening for inserting an object to be examined, and a plurality of spoke portions that connect the hollow cylinder portion and the ring portion, and
wherein the spoke portions of both sides of the X-ray tube include a portion in which the thickness in the direction of a rotation axis is thicker than those of the other spoke portions.

7. The X-ray CT apparatus according to claim 1,
wherein a plurality of the spoke portions include spoke portions of a plurality of kinds in which the cross-sectional shapes are different in the direction perpendicular to the radial direction of the cylinder portion.

8. An X-ray CT apparatus comprising an X-ray tube, an X-ray detection unit, one or more circuit units, and a rotating portion on which the X-ray tube, the X-ray detection unit, and one or more circuit units are mounted to be rotated,
wherein the rotating portion includes a hollow cylinder portion in which the X-ray tube and one or more circuit units are fixed on an inner wall thereof, a ring portion on which the X-ray detection unit is fixed and that has an opening into which an object is inserted, and a plurality of spoke portions that connect the hollow cylinder portion and the ring portion, and
wherein the ring portion includes a region in which the width is wider than the remainder of the ring portion, and the X-ray detection unit is mounted on the region.

9. The X-ray CT apparatus according to claim 2,
wherein the X-ray tube and one or more circuit units are constituted so that each end thereof is inserted into an opening between the spoke portions.

10. An X-ray CT apparatus comprising an X-ray tube, an X-ray detection unit, one or more circuit units, and a rotating portion on which the X-ray tube, the X-ray detection unit, and one or more circuit units are mounted to be rotated,
wherein the rotating portion includes a hollow cylinder portion in which the X-ray tube and one or more circuit units are fixed on an inner wall thereof, a ring portion on which the X-ray detection unit is fixed and that has an opening into which an object is inserted, and a plurality of spoke portions that connect the hollow cylinder portion and the ring portion, and
wherein the spoke portions of both sides of the X-ray tube include a portion in which the thickness in the direction of a rotation axis is thicker than those of the other spoke portions.

* * * * *